United States Patent [19]

Theodoropulos

[11] Patent Number: 4,780,535
[45] Date of Patent: Oct. 25, 1988

[54] MALEIC AND PHTHALIC DIAMIDES

[76] Inventor: Spyros Theodoropulos, 2964 Hickory St., Yorktown Heights, N.Y. 10598

[21] Appl. No.: 933,168

[22] Filed: Nov. 21, 1986

[51] Int. Cl.$^4$ .................. C07D 265/28; C07D 237/32
[52] U.S. Cl. .................................. 544/99; 544/103;
549/225; 562/442; 562/450; 564/153; 564/156; 564/160
[58] Field of Search ................. 544/99, 103; 549/225; 562/442, 450; 564/153, 156, 160

[56] References Cited

U.S. PATENT DOCUMENTS

| | | | |
|---|---|---|---|
| 2,998,425 | 8/1961 | Sauers et al. | 549/321 |
| 4,179,466 | 12/1979 | Bollinger et al. | 564/156 X |
| 4,433,154 | 2/1984 | Hirai | 564/156 X |
| 4,600,775 | 7/1986 | Theodoropulos | 544/99 |

Primary Examiner—Richard L. Raymond
Attorney, Agent, or Firm—Burgess, Ryan and Wayne

[57] ABSTRACT

Conjugates of isomaleimides and isophthalimides and organic chromophoric compounds exhibiting fluorescence, luminescence, chemiluminescence or absorption of analytical value having the structural formula I and II

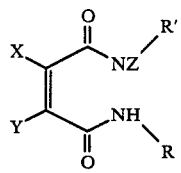

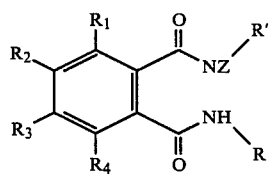

wherein R is an organic aromatic molecule which may be substituted, heteroaromatic which may be substituted, aliphatic having 1 to 50 carbon atoms and which may be substituted or an organic chromophoric molecule exhibiting fluorescence, luminescence, chemiluminescence or absorption of analytical value. R' is an organic chromophoric molecule exhibiting fluorescence, luminescence, chemiluminescence, or absorption of analytical value; $R_1$ is hydrogen, halogen, carboxylic, alkyl, aryl, hydroxyl, amino group which may be substituted, nitro or sulfonic group. $R_2$, $R_3$ and $R_4$ have the same meaning as $R_1$; X is hydrogen, alkyl, aryl, halogen, carboxylic, alkoxy, aryloxy, hydroxyl, amino group which may be substituted or alkyl group forming a five or six member ring with the adjacent olefinic carbon atom; Y has the same meaning as X; Z is hydrogen, alkyl having 1 to 18 carbon atoms or aryl. The maleic diamides and the phthalic diamides of the invention may be used for the labeling of organic substrates as staining materials and as indicators.

9 Claims, No Drawings

MALEIC AND PHTHALIC DIAMIDES

FIELD OF THE INVENTION

This invention relates to novel maleic and phthalic diamides and more particularly this invention relates to conjugates of isomaleimides and isophthalimides and chromophoric compounds forming maleic and phthalic diamides of which one or both of the amino moieties is a chromophoric compound of interest.

BACKGROUND OF THE INVENTION

A variety of chromophors exhibiting fluoresence, chemiluminescence, luminescence or absorption of analytical value, can be derivatized to maleic or phthalic diamides. The maleic or phthalic moiety of the chromophoric compounds contributes to the photochemical stability retarding the bleaching effect of ultraviolet light. Furthermore, the maleic or phthalic moiety so produced has an effect on the basic characteristics of certain classes of chromophors resulting in chromophors with superior characteristics.

The novel compounds are intended for use in analytical techniques for the detection and measurement of biological and clinical compounds of interest. Typical examples of such components are bacteria, viruses, enzymes, blood groups, drugs and hormones.

It is known that fluorescent groups such as fluorescein have been used in a variety of analytical techniques for the detection and measurement of biological compounds of interest. Analytical techniques employing fluorescein or fluorescent derivatives such as for example fluorescein isothiocyanate do undergo bleaching when exposed to ultraviolet light resulting quickly to loss of fluoresence.

Accordingly, it is an object of the present invention to provide maleic or phthalic diamides of chromophors exhibiting superior stability over the native chromophors.

A further object of this invention is to provide novel maleic or phthalic diamide derivatives of chromophors which will exhibit distinct fluoresence excitation and emission spectra, corresponding to that of the specific class of chromophors.

While the invention is susceptible to various modifications and alternative forms, the preferred embodiments will be described in detail. It is not intended to limit the invention to the specific forms disclosed. On the contrary, it is intented to cover all modifications and alternative forms falling within the spirit and scope of the invention as expressed in the appended claims.

SUMMARY OF THE INVENTION

The present invention is directed to novel maleic and phthalic diamides of chromophoric molecules. The maleic and phthalic moieties allow for photochemical stability and the rise of chromophors with interesting and distinct fluorescence excitation and emission spectra.

The basic structure of the maleic and phthalic diamides are structurally represented by the structural formulas I and II.

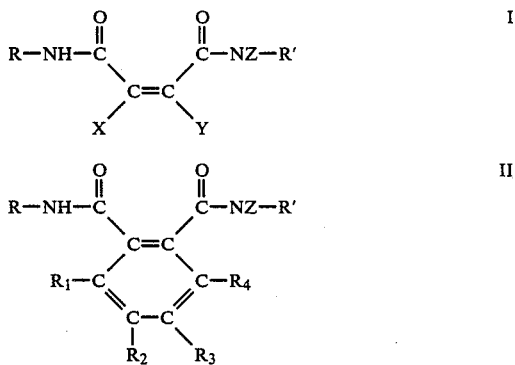

wherein $R'$ is an organic group containing up to 50 carbon atoms and which exhibits chromophoric characteristics of analytical value; R is an aliphatic, aromatic or heteroaromatic group containing up to 50, preferably up to 28, and still more preferably up to 12 carbon atoms, and which itself may or may not exhibit chromophoric properties which can be the same or different from $R'$; or R itself can represent the above structural moiety I or II to which R is attached, and thus provide a dimer; Z is hydrogen or alkyl or aryl having up to 18 carbon atoms; X is hydrogen, alkyl, aryl, amino, alkylamino or arylamino, halogen, mercapto, hydroxyl, alkoxy, aryloxy, carboxylic or alkyl forming a cyclic five or six member ring with the adjacent olefinic carbon atoms and can contain up to 18 carbon atoms, preferably up to 12; Y has the same meaning as X; and $R_1$ $R_2$, $R_3$ and $R_4$ are hydrogen, halogen, hydroxyl, amino, nitro, sulfonic or alkyl, aryl, carboxylic, alkoxy or aryloxy of up to 18 carbon atoms.

Typical examples of maleic or phthalic diamides of chromophoric compounds are shown below, both by structural formula and name.

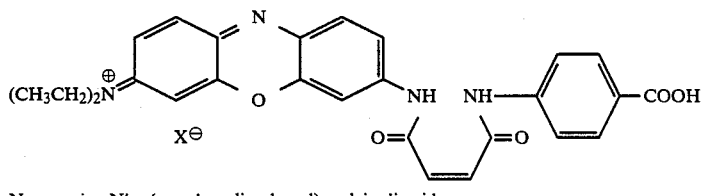

N—oxazine-N'—(p-carboxylic phenyl)-maleic diamide

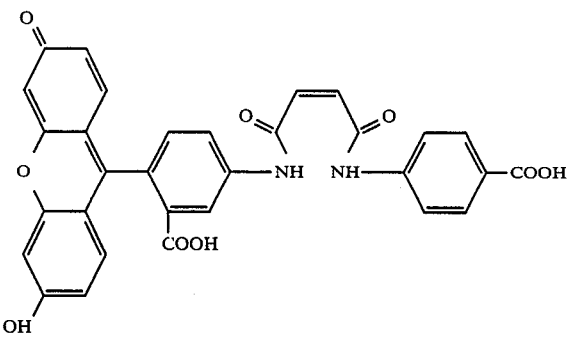

N—Fluoresceinyl-N'—(p-carboxylic phenyl)-maleic diamide

DETAILED DESCRIPTION OF THE INVENTION

The maleic and phthalic diamide compounds of the invention are exhibiting unique characteristics very important in the field of clinical chemistry. The maleamide or the phthalamide moieties add photochemical stability to the chromophors and can be used to introduce reactive functionalities well suited for further attachment to substrates of interest. Furthermore, the maleamide or phthalamide derivatization produces chromophors with very distinct characteristics attributed to maleic or phthalic moieties.

N-p-carboxyphenyl-N'-oxazine-maleic diamide, for example, shows an excitation of about 500 nm and emission of about 600 nm, while the native chromophor exhibits and excitation at about 600 nm and an emission at 630 nm. The carboxyl moiety of the same serves for the attachment of the chromophor to proteins and other organic molecules of interest. Fluorescein or fluorescein isothiocyanate, a readily-available chromophor has been found to undergo rapid bleaching or loss of fluorescence when exposed to ultraviolet light. In contrast, the maleamide or phthalamide derivatives of fluorscein exhibit superior stability to ultraviolet light undergoing little or no bleaching.

The maleic and phthalic diamide compounds of the invention represented structurally as IA and IIA where synthesized in two steps using known techniques.

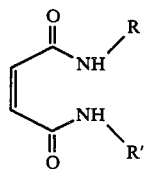

IA

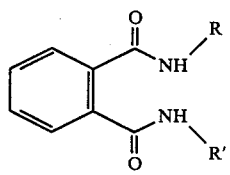

IIA

In the first step an organic molecule having a primary amino group or an isocyanato group has been derivatized to the isomaleimide or isophthalimide using the techniques described in the literature.

In the second step, an isomaleimido or isophthalimido compound so derived was allowed to react with a chromophoric compound having an active amino group to form the maleic or phthalic diamide.

Two examples illustrating the conjugation of an oxazine chromophor with p-isomaleimido-benzoic acid and p-isophthalimido-benzoic acid are shown in the equation I and II respectively.

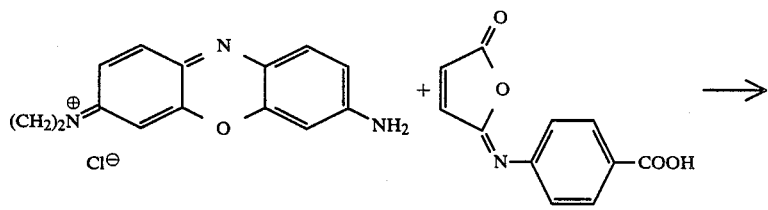

I

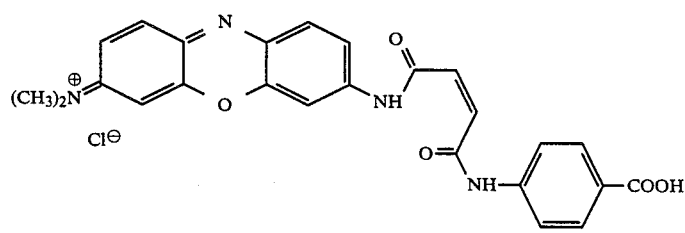

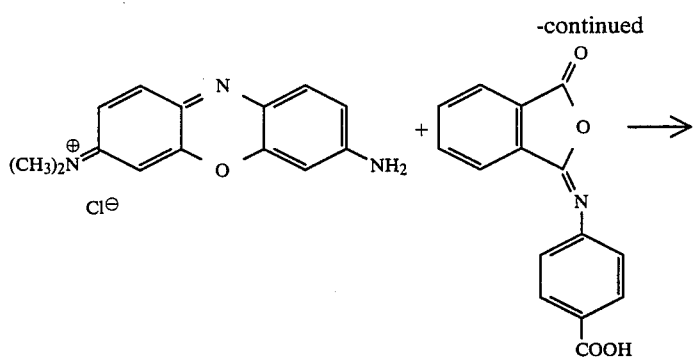

II

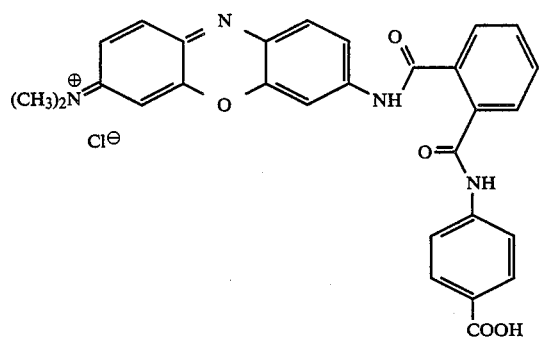

In its broadest aspect, the process by which the maleic or phthalic diamides of the present invention are prepared by reacting the isomaleimide or the isophthalimide having the general formula I and II

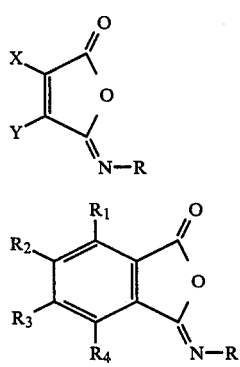

wherein R is an organic molecule aromatic which may be substituted or aliphatic having 1 to 50 carbon atoms and which may be subsituted; X is hydrogen, halogen, carboxylic, alkyl, aryl, alkoxy, aryloxy, hydroxyl, mercapto, alkylamino or arylamino; Y has the same meaning as X; $R_1$ is hydrogen, halogen, carboxylic, alkoxy or aryloxy, $R_2$, $R_3$ and $R_4$ have the same meaning as $R_1$; with a chromophoric compound having an active amino group.

The reaction between an isomaleimido such as IB and an isophthalimido compound such as IIB and a chromophoric compound represented by the general formula III.

R'NHZ     III wherein R' is a chromophoric compound exhibiting fluorescence, chemiluminescence or absorption of analytical value and Z is hydrogen, alkyl having 1 to 18 carbon atoms or aryl; is represented by the equation 1 and 2 respectively.

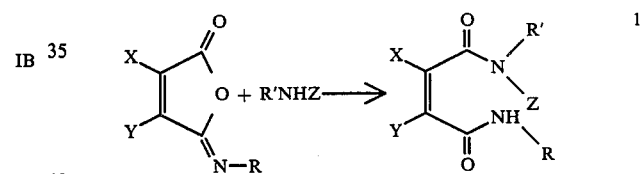

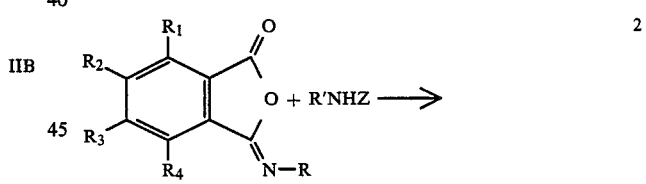

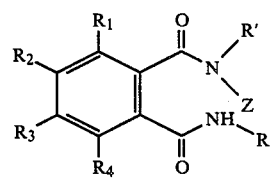

As a general rule maleic or phthalic diamides can be prepared by the conjugation of an isomaleimide or isophthalimide and a chromophor having a reactive amino group. This rule should, however, allow for the conjugation of organic compounds having more than one isomaleimido or isophthalimido moieties with chromophoric compounds. As is the case many compounds having more than one primary amino groups can be derivatized to compounds having two or more isomaleimido or isophthalimido moieties. Two examples illustrating the conjugation of 5-aminofluorescein with 3,5-diisomaleimido-benzoic acid and bis- isomaleimide are shown in equations III and IV, respectively.

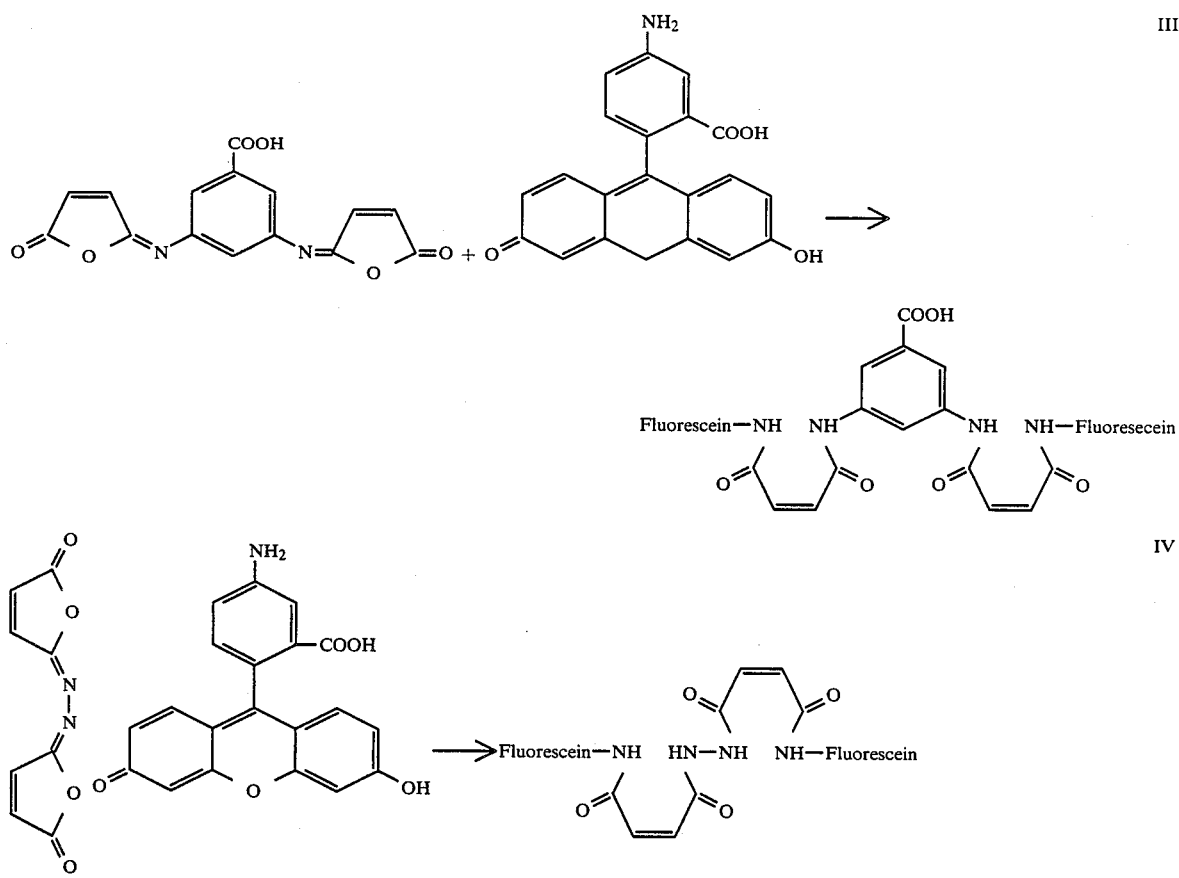

The maleic or phthalic diamides of chromophoric compounds described in this invention can be used to label biological molecules of clinical interest, for the preparation of fluorescent microbeads, as intercalating fluorescent agents or as staining materials for the staining of cells and as indicators.

The chromophoric compounds of the present invention can be conveniently coupled to an inert matrix or organic substrate by known techniques to provide the conjugate.

For example, the chromophoric compounds can be coupled to a wide variety of biologically acceptable substrates which are normally employed in the detection and measurement of biological compounds. The only requirement of the matrix or substrate is that it contain one or more active sites through which coupling with the chromophoric derivative can be effected. In practice, such sites usualy contain an active hydrogen and include, but are not limited to, primary amines, secondary amines, hydroxyl groups, mercapto groups and the like. As indicated coupling of the chromophoric derivative to the matrix or substrate is effected by methods known to those skilled in the art to which this invention pertains.

It is therefore possible to form conjugates of the chromophoric derivatives with a wide variety of organic substrates, including, drugs, antigens, antibodies, haptens, peptides, proteins, amino acids, enzymes, and the like. A particularly preferred inert substrate which is widely used in the detection and measurement of biological compounds is the spherical beads employed in chromatographic techniques. For example, the derivatives of this invention can be conveniently enclosed in small beads such as those composed of polystyrene or other inert biological compositions.

The chromophoric derivatives of the present invention are therefore useful in a wide variety of areas as a biochemical tool for the detection and measurement of biological compounds. For example, the derivatives can be employed as conjugates with and inert matrix or organic substrate for use in antigen-antibody assays. Molecules, such as fluorescein or rhodamine are currently employed for fluorescence microscopy in indirect immunocytochemistry. Due to their improved stability, resistance to bleaching and the wide spread between excitation and emission the derivatives of the present invention are ideally suited for replacement of the fluorescein currently employed in fluorescent antibodies.

The derivatives of the present invention are also useful in conjunction with SDS gel electrophoresis for the study of peptide fragments from the cleavage of proteins. In such studies, chromatography and electrophoresis provide a 2-dimensional map or "fingerprint" diagnostic of a protein.

The chromophoric derivatives of the present invention are also useful as a replacement for radioactive tracers in automated electrophoresis processes such as those employed in determining the sequence of nucleic acids of genes. Newly available analytical instruments, such as the DNA sequencer, developed at the California Institute of Technology are currently in use to expedite gene mapping of strnads of DNA. In the current version of these instruments a laser and fluorescent dyes replace the use of radioactive materials and result in markedly increased savings in the time needed to effect the mapping. In the DNA sequencer amino acids exposed to intense light cause the dye to glow. By computer analysis of the intensity and color, the identity of the nucleic acid base can be determined. The chromophoric derivatives of the present invention are particularly attractive for this application due to their stability in the presence of high intensity light such as the lasers employed in the DNA sequencer, and the distinct wide spread between the points of excitation and emission. Additionally, as previously indicated, the derivatives of the present invention are resistant to bleaching and hence are ideally suited for this application.

EXAMPLE 1

PREPARATION OF N-CRESYL VIOLET-N'-(P-CARBOXYLICPHENYL)-MALEIC DIAMIDE

A mixture of 321 milligrams of cresyl violet and 350 milligrams of p-isomaleimido-benzoic acid in 10 milliliters of acetic acid was stirred at ambient temperature for 5 days. Ultraviolet absorption of the reaction mixture showed a major shift from 580 nm to 480 nm indicating maleic diamide formation. The solvent was removed under reduced pressure and the product was purified by column chromatography on silica gel using ether, methanol and acetic acid as the eluent solvents. 220 milligrams of the maleic diamide was obtained. Ultraviolet absorption spectra in methanol showed maxima at 470 nm. Fluorescence spectra in water showed:

Excitation (pH 5) 507 nm. Emission (pH 5) 588 and 621 nm.

Excitation (pH 8) 507 nm. Emission (pH 8) 600 nm.

EXAMPLE 2

PREPARATION OF N-FLUORESCEINYL-N'-(P-CARBOXYLIC-PHENYL)-MALEIC DIAMIDE

A mixture of 50 milligrams of 5-amino fluorescein and 150 milligrams of p-isomaleimido-benzoic acid in 2.0 ml of glacial acetic acid was stirred at ambient temperature until the red aminofluorescein was converted to the yellowish diamide (about 24 hours). The product was filtered and washed with acetic acid and ether. 72 Milligrams of n-fluoresceinyl-n'-(p-carboxylicphenyl)-maleic diamide was obtained.

EXAMPLE 3

PREPARATION OF N-NILE BLUE-N'-(P-CARBOXYLIC-PHENYL)-MALEIC DIAMIDE

A mixture of 353 milligrams of Nile Blue A, 500 milligrams of p-isomaleimido-benzoic acid and 200 milligrams of lithium acetate in 2.0 ml of galcial acetic acid was stirred at ambient temperature for three days. The solvent was removed under reduced pressure and the product was purified by column chromatography on silica gel. The product was eluded with 10% acetic acid in methanol.

Fluorescence spectra in dimethylformamide showed: Ex 510 nm; Em 580 nm.

EXAMPLE 4

PREPARATION OF N-CRESYL VIOLET-N'-(4-CARBOXYMETHYLPHENYL)-MALEIC DIAMIDE

A mixture of 620 milligrams of cresyl violet acetate and 750 milligrams of p-isomaleimidophenyl acetic acid in 10 milliliters of dry dioxane was stirred at 70° C. for 24 hours or until the absorption of the reaction mixture had shifted from 590 nm to 500 nm.

The solvent was removed under reduced pressure. The product was purified by column chromatography on silica gel using 10% acetic acid in methanol.

Ultraviolet absorption spectra showed maximum at 490 nm in methanol.

EXAMPLE 5

PREPARATION OF N-CRESYL VIOLET-N'-(4-HYDROXY-1-ANTHRAQUINOLYL)-MALEIC DIAMIDE

A mixture of 160 milligrams of cresyl violet acetate and 200 milligrams of 1-isomaleimido-4-hydroxy-anthraquinone in 5 milliliters of dioxane was stirred at 70° C. for 16 hours. The solvent was removed under reduced pressure and the product was washed with ether.

Ultraviolet absorption spectra showed maximum at 490 nm in methanol.

What is claimed is:

1. A compound selected from the group consisting of:

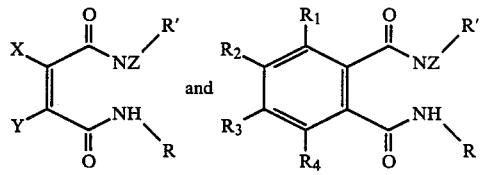

wherein R is an organic aliphatic, aromatic or heteroaromatic group having up to 28 carbon atoms, an organic chromophoric group exhibiting fluorescence, luniescence, chemiluminescence or absorption properties, or R can itself represent the remainder of the molecule to which it is attached to provide a dimer; R' is an organic chromophoric group exhibiting fluorescence, luminescence, chemiluminescence or absorption properties, X and Y are hydrogen, alkyl, aryl, halogen, carboxylic, alkoxy, aryloxy, hydroxyl, amino; alkylamino, arylamino or mercapto or X and Y taken together are an alkylene group forming a five or six member ring with the adjacent carbon atoms to which they are attached; $R_1$, $R_2$, $R_3$ and $R_4$ are hydrogen, halogen, hyroxyl, amino, nitro, sulfonic or alkyl, aryl, carboxylic, alkoxy or aryloxy groups of up to 18 carbon atoms; and Z represents hydrogen, alkyl or aryl having up to 18 carbon atoms.

2. The compound of claim 1 having the formula

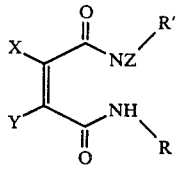

wherein R, R', $R_1$, $R_2$, $R_3$, $R_4$, X, Y and Z are as indicated.

3. The compound of claim 1 having the formula

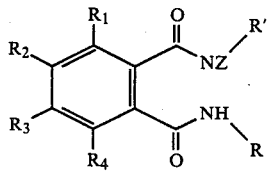

wherein R, R', $R_1$, $R_2$, $R_3$, $R_4$, X, Y and Z are as indicated.

4. Conjugates of bis-isomaleimides and a chromophor exhibiting fluorescence, chemiluminescence, luminescence and absorption of analytical value having the formula:

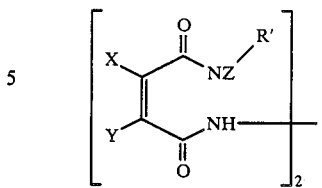

wherein R', X, Y and Z are the same as described in claim 1.

5. Conjugates of bis-isophthalimides and a chromophor exhibiting fluorescence, luminescence, chemiluminescence or absorption of analytical value having the formula:

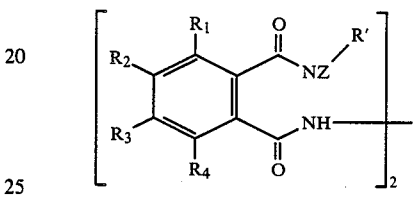

wherein $R_1$, $R_2$, $R_3$, $R_4$, and Z are the same as described in claim 1.

6. The compound of claim 1 wherein at least one of R or R' exhibits fluorescence properties.

7. The compound of claim 1 wherein at least one of R or R' exhibits luminescence properties.

8. The compound of claim 1 wherein at least one of R or R' exhibits chemiluminescence properties.

9. The compound of claim 1 wherein at least one of R or R' exhibits absorption properties.

* * * * *